April 4, 1961 F. W. ANDERSON Plant Pat. 2,043

PLUM TREE

Filed July 5, 1960

WITNESS

Addison E Avery

INVENTOR

Frederic W. Anderson

Webster & Webster

ATTYS.

United States Patent Office

Plant Pat. 2,043
Patented Apr. 4, 1961

2,043

PLUM TREE

Frederic W. Anderson, Merced, Calif., assignor to Kim Bros., a copartnership doing business under the fictitious name and style of Reedley Nursery, Reedley, Calif.

Filed July 5, 1960, Ser. No. 40,981

1 Claim. (Cl. 47—62)

The present invention relates to a new and distinct variety of plum tree which bears large, firm, globose, freestone fruit having cream-colored flesh and a deep blue exterior color shaded with a dark red, giving a general over-all purple-blue appearance.

At present the leading commercially grown shipping varieties, which are in harvest immediately following the Santa Rosa, are the Burbank, Duarte, Nubiana, and Laroda.

In comparison, and which characterizes its essential novelty, the fruit of the present variety is larger, firmer, more attractive in appearance, and has more exterior color than the Burbank; is larger, and brighter in exterior color than the Duarte, with cream instead of red colored flesh, and globose instead of conical in shape; is larger, and ripens several days earlier than the Nubiana with more red in the blue exterior color, and globose instead of oblate in shape; and is larger, and ripens at least a week earlier than the Laroda with more red in the blue exterior color, and self-fertile instead of self-sterile.

The herein claimed variety of plum tree was originated by me, in my experimental orchard located near Merced, California, as a selected seedling from a large number thereof obtained from El Dorado plug seeds that had resulted from open-pollinated flowers.

Such large number of seedlings, which were grown under careful observation by me, reflected—when they came into bearing—many and varying characteristics; one of such seedlings, and which is the present variety, having been especially desirable with respect to its fruit characteristics, and I therefore selected such seedling for asexual reproduction and commercialization.

Subsequent to its origination and selection by me asexual reproduction of the variety was successfully accomplished by topworking on mature nectarine trees in my experimental orchard located as aforesaid; the reproductions having run true to the parent in every respect.

Figure 1:
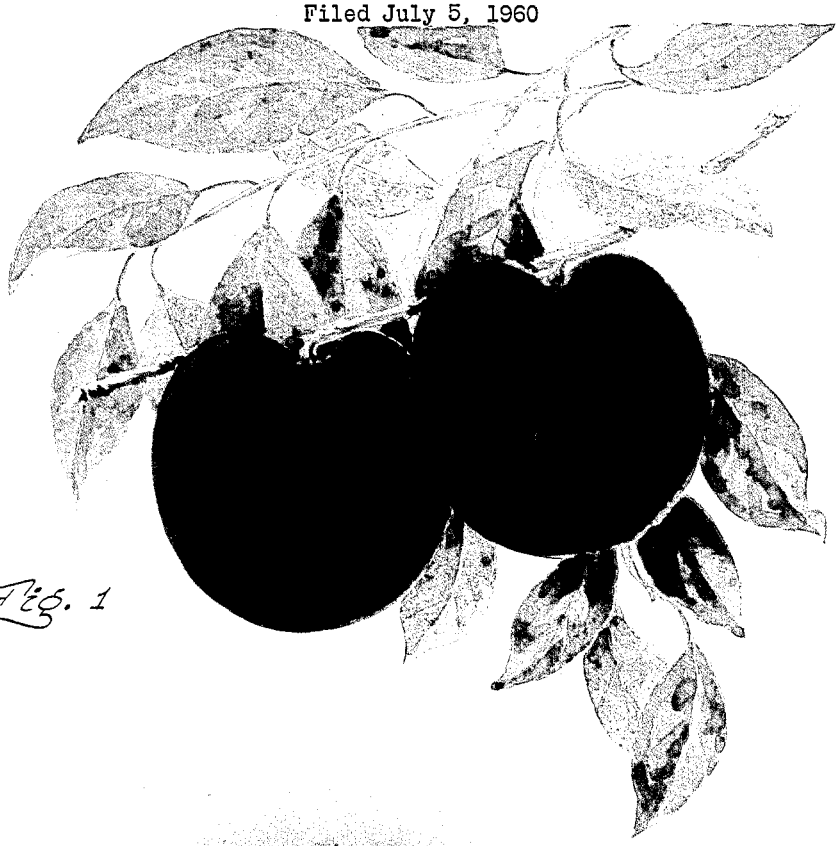
Fig. 1 is an elevation showing two of the plums, together with twigs and leaves.
Figure 2:
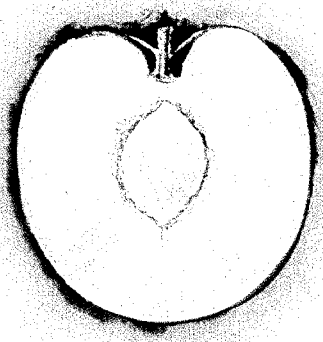
Fig. 2 is a sectional elevation of one of the plums, with the stone remaining in place.

Referring now more specifically to the pomological details of this new and distinct variety of plum tree, the following is an outline description thereof; all major color plate identifications being by reference to Maerz and Paul Dictionary of Color, except where common terms of color definition are employed.

Tree:
- *Size.*—Medium
- *Vigor.*—Medium.
- *Form.*—Spreading.
- *Production.*—Productive.
- *Bearing.*—Regular bearer.

Trunk:
- *Size.*—Medium.
- *Bark.*—Medium

Branches:
- *Size.*—Medium.
- *Bark.*—Smooth.

Leaves:
- *Size.*—Medium. Average length—2⅝". Average width—1 7/16".
- *Form.*—Oval; abruptly pointed.
- *Thickness.*—Medium.
- *Margin.*—Crenate.
- *Petiole.*—Medium thickness.
- *Glands.*—Average number and position.—usually two at base of blade. Small.
- *Color.*—Top side—medium green (22–L–6 to 23–L–5). Under side—lighter green (22–F–6).

Flower buds:
- *Size.*—Medium.
- *Length.*—Medium.
- *Form.*—Conic.

Flowers:
- *Blooming period.*—Approximately with the Santa Rosa; medium as compared with other varieties.
- *Size.*—Medium.
- *Color.*—White.

Fruit:
- *Maturity when described.*—Eating ripe, July 20, 1959.
- *Date of first picking.*—July 10, 1959.
- *Date of last picking.*—July 25, 1959.
- *Size.*—Uniform; large. Average diameter axially—2⅜". Average transversely in suture plane—2¼".
- *Form.* — Uniform; symmetrical; globose, some slightly ovoid.
- *Suture.*—Distinct.
- *Ventral surface.*—Rounded slightly.
- *Cavity.*—Rounded.—Average depth—7/16". Average breadth—¾".
- *Base.*—Rounded.
- *Apex.*—Short.

Skin:
- *Thickness.*—Thick to medium.
- *Texture.*—Medium.
- *Tendency to crack.*—None.
- *Color.*—Deep blue (40–L–12) shaded with a dark red (56–L–12), giving a general over-all purple-blue appearance.

Flesh:
- *Texture.*—Firm; fine; crisp; meaty; melting.
- *Ripens.*—Even.
- *Flavor.*—Delicate; vinous.
- *Eating quality.*—Good to best.
- *Color.*—Cream (10–F–3), shading darker (11–G–4 to 12–D–4).

Stone:
- *Type.*—Free.
- *Size.* — Small. Average length — ¾". Average breadth—⅝". Average thickness—⅜".
- *Form.*—Oval.
- *Base.*—Straight.
- *Apex.*—Rounded.
- *Sides.*—Equal
- *Ventral edge.*—Thin.
- *Dorsal edge.*—Full, with broad groove.
- *Tendency to split.*—None.
- *Color.*—Maize (10–D–6), shading in part somewhat darker (10–D–8).

Use: Market; long distance shipping.
Keeping quality: Good.
Shipping quality: Good.

All of the prior varieties of plum trees as hereinbefore identified are unpatented.

The tree and its fruit herein described may vary in slight detail due to climatic and soil conditions under which the variety may be grown; the present description being of the variety as grown in the Central Valley of California.

The following is claimed:

A new and distinct variety of plum tree, as illustrated and described, which bears large, firm, globose, freestone fruit having cream-colored flesh, and a deep blue exterior color shaded with a dark red, giving a generally over-all purple-blue appearance; said fruit—in comparison—being larger, firmer, more attractive in appearance, and having more exterior color than the Burbank; being larger, and brighter in exterior color than the Duarte, with cream instead of red colored flesh, and globose instead of conical shape; being larger, and ripening several days earlier than the Nubiana with more red in the blue exterior, and globose instead of oblate shape; and being larger, and ripening at least a week earlier than the Laroda with more red in the blue exterior color, and self-fertile instead of self-sterile.

No references cited.